(12) United States Patent
Mullan

(10) Patent No.: US 7,538,258 B2
(45) Date of Patent: May 26, 2009

(54) TRANSGENIC MOUSE EXPRESSING AN APP 670/671 MUTATION

(75) Inventor: Michael John Mullan, Tampa Palms, FL (US)

(73) Assignee: Alzheimer's Institute of America, Inc., Mission Hills, KS (US)

( * ) Notice: Subject to any disclaimer, the term of this patent is extended or adjusted under 35 U.S.C. 154(b) by 139 days.

(21) Appl. No.: 11/715,632

(22) Filed: Mar. 8, 2007

(65) Prior Publication Data

US 2007/0169207 A1 Jul. 19, 2007

Related U.S. Application Data

(60) Continuation of application No. 10/978,713, filed on Nov. 1, 2004, now abandoned, which is a continuation of application No. 09/785,951, filed on Feb. 16, 2001, now Pat. No. 6,818,448, which is a continuation of application No. 09/058,384, filed on Apr. 9, 1998, now abandoned, which is a continuation of application No. 08/808,126, filed on Feb. 28, 1997, now abandoned, which is a continuation of application No. 08/478,197, filed on Jun. 7, 1995, now abandoned, which is a division of application No. 08/094,547, filed on Feb. 19, 1993, now abandoned, which is a continuation of application No. 07/894,211, filed on Jun. 4, 1992, now Pat. No. 5,455,169.

(51) Int. Cl.
*A01K 67/033* (2006.01)
*G01N 33/00* (2006.01)

(52) U.S. Cl. .................. 800/12; 800/18; 800/3

(58) Field of Classification Search .............. None
See application file for complete search history.

(56) References Cited

U.S. PATENT DOCUMENTS 5,455,169 A 10/1995 Mullan

OTHER PUBLICATIONS

Lannfelt et al. Alzheimer's Disease: Molecular Genetics and Transgenic Animal Models. Behav. Brain Res., 1993, vol. 57, pp. 207-213.*
Selkoe, D. In the Beginning ... Nature. 1991, vol. 354, pp. 432-433.*
Higgins et al. Transgenic mice expressing human beta-APP751, but not mice expressing beta-APP695, display early Alzheimer's disease-like histopathology. Annals NY Acad. Sci. 1993, vol. 695, pp. 224-227.*
Felsenstein et al. Transgenic Rat and In-Vitro Studies of β-Amyloid Precursor Protein Processing. Hanin, I. et al., eds., Advances in Behavioral Biology: Alzheimer's and Parkinson's diseases: Recent developments. Publisher: Plenum Press, 1995, pp. 401-405.*

Kappel et al (1992) Regulating Gene Expression in Transgenic Animals, Current Opinion in Biotechnology, vol. 3, 548-553.*
Andra et al. "Expression of APP in Transgenic Mice: A Comparison of Neuron-Specific Promoters." *Neurobiol. Aging* 17(2):183-190 (1996).
*Elan Pharmaceuticals., Inc.* v. *Mayo Foundation for Medical Education* 304 F.3d 1221, 1220-1235 (Fed. Cir. 2002).
Forss-Petter et al. "Transgenic Mice Expressing β-Galactosidase in Mature Neurons under Neuron-Specific Enolase Promoter Control." *Neuron* 5:187-197 (1990).
Felsenstein, et al., "Transgenic Rat and In-Vitro Studies of β-Amyloid Precursor Protein Processing. Hanin, I. et al., eds., Advances in Behavioral Biology: Alzheimer's and Parkinson's diseases: Recent developments." *Publisher: Plenum Press*, pp. 401-405 (1995).
Greenberg et al. "APP Transgenesis: Approaches Toward the Development of Animal Models for Alzheimer Disease Neuropathology." *Neurobiol. Aging* 17(2):153-171 (1996).
Higgins, et al., "Transgenic mice expressing human β-APP751, but not mice expressing β-APP695, display early Alzheimer's disease-like histopathology." *Annals NY Acad. Sci.* 695:224-227 (1993).
Hsiao et al. "Correlative Memory Deficits, Aβ Elevation, and Amyloid Plaques in Transgenic Mice." *Science* 274:99-102 (1996).
Hsiao et al. "Measuring Memory in a Mouse Model of Alzheimer's Disease." *Science* 277:839-841 (1997).
Kappel, et al., Regulating Gene Expression in Transgenic Animals, *Current Opinion in Biotechnology* 3:548-553 (1992).
Lannfelt, et al., "Alzheimer's Disease: Molecular Genetics and Transgenic Animal Models." *Behav. Brain Res.*, 57:207-213 (1993).
Malherbe et al. "Lack of β-Amyloidosis in Transgenic Mice Expressing Low Levels of Familial Alzheimer's Disease Missense Mutations," *Neurobiol. Aging* 17(2):206-214 (1996).
Selkoe, D., "In the Beginning ... " *Nature*, 354:432-433 (1991).
Sturchler-Pierrat et al. "Two amyloid precursor protein transgenic mouse models with Alzheimer disease-like pathology." *Proc. Natl. Acad. Sci. USA* 94:13287-13292 (1997).
Yehiely et al. "Identification of Candidate Proteins Binding to Prion Protein." *Neurobiol. Disease* 3:339-355 (1997).
Zhao et al. "β-Secretase Processing of the β-Amyloid Precursor Protein in Transgenic Mice is Efficient in Neurons but Inefficient in Astrocytes." *J. Biological Chem* 271(49):31407-31411 (1996).

* cited by examiner

*Primary Examiner*—Deborah Crouch
(74) *Attorney, Agent, or Firm*—Ballard Spahr Andrews & Ingersoll, LLP

(57) ABSTRACT

The invention provides an isolated nucleic acid characteristic of human amyloid precursor protein 770 including the nucleotides encoding codon 670 and 671, wherein the nucleic acid encodes an amino acid other than lysine at codon 670 and/or an amino acid other than methionine at codon 671. Also provided is a method of diagnosing or predicting a predisposition to Alzheimer's disease, comprising detecting in a sample from a subject the presence of a mutation at a nucleotide position corresponding to codons 670 and/or 671 of amyloid precursor protein or fragment thereof, the presence of the mutation indicating the presence of or a predisposition to Alzheimer's disease.

6 Claims, 1 Drawing Sheet f144 f139

SEQUENCE LISTING

```
<160> NUMBER OF SEQ ID NOS: 3

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence; note =
      Synthetic Construct
<220> FEATURE:
<221> NAME/KEY: variation
<222> LOCATION: (4)...(5)
<223> OTHER INFORMATION: Xaa = can be any amino acid except Lys and/or
      Xaa = can be any amino acid except Met

<400> SEQUENCE: 1

Ser Glu Val Xaa Xaa Asp Ala Glu
  1               5

<210> SEQ ID NO 2
<211> LENGTH: 44
<212> TYPE: DNA
<213> ORGANISM: Artificial Sequence
<220> FEATURE:
<223> OTHER INFORMATION: Description of Artificial Sequence; note =
      Synthetic Construct

<400> SEQUENCE: 2
cagactgaga tcccagaacc ctaggtctga ctctagggtc ttgg                    44

<210> SEQ ID NO 3
<211> LENGTH: 48
<212> TYPE: DNA
<213> ORGANISM: Artificial Sequence
<220> FEATURE:
<223> OTHER INFORMATION: Description of Artificial Sequence; note =
      Synthetic Construct

<400> SEQUENCE: 3
cagactgaga tcccagaacc gatcctaggt ctgactctag ggtcttgg                48
```

TRANSGENIC MOUSE EXPRESSING AN APP 670/671 MUTATION

CROSS-REFERENCE TO RELATED APPLICATIONS

This application is a continuation of co-pending U.S. application Ser. No. 10/978,713, filed Nov. 1, 2004, which is a continuation of U.S. application Ser. No. 09/785,951, filed Feb. 16, 2001 (now U.S. Pat. No. 6,818,448, issued Nov. 16, 2004), which is a continuation of U.S. application Ser. No. 09/058,384, filed Apr. 9, 1998 (abandoned), which is a continuation of U.S. application Ser. No. 08/808,126, filed Feb. 28, 1997 (abandoned), which is a continuation of U.S. application Ser. No. 08/478,197, filed Jun. 7, 1995 (abandoned), which is a divisional of U.S. application Ser. No. 08/094,547, filed Feb. 19, 1993 (abandoned), which is a continuation of U.S. application Ser. No. 07/894,211, filed Jun. 4, 1992 (now U.S. Pat. No. 5,455,169, issued Oct. 3, 1995), which applications are hereby incorporated herein by reference in their entireties.

BACKGROUND OF THE INVENTION

Alzheimer's disease (AD) is a progressive disease known generally as senile dementia. Broadly speaking, the disease falls into two categories, namely late onset and early onset. Late onset, which occurs in old age (65+ years), may be caused by the natural atrophy of the brain occurring at a faster rate and to a more severe degree than normal. Early onset AD is much more infrequent but shows a pathologically identical dementia with diffuse brain atrophy which develops well before the senile period, i.e., between the ages of 35 and 60 years. There is evidence that one form of this type of AD shows a tendency to run in families and is therefore known as familial Alzheimer's disease (FAD).

In both types of AD the pathology is the same but the abnormalities tend to be more severe and more widespread in cases beginning at an earlier age. The disease is characterized by two types of lesions in the brain: senile plaques and neurofibrillary tangles.

Senile plaques are areas of disorganized neuropil up to 150 mm across with extra cellular amyloid deposits at the center. Neurofibrillary tangles are intracellular deposits of amyloid protein consisting of two filaments twisted about each other in pairs.

The major protein subunit, B-amyloid protein (also referred to in the art as amyloid B protein (ABP) and A4) of the amyloid filaments of both the neurofibrillary tangle and the senile plaque, is a highly aggregating small polypeptide of approximate relative molecular mass 4,500. This protein is a cleavage product of a much larger precursor protein called amyloid precursor protein (APP).

The sequence of the deposited B-amyloid protein in particular brain regions-is one of the main pathologic characteristics of AD. The β-amyloid protein is an approximately 4 kD protein (39 to 42 amino acids) which is derived, as an internal cleavage product, from one or more isoforms of a larger APP. There are at least five distinct isoforms of APP: 563, 695, 714, 751, and 770 amino acids, respectively (Wirak et al. (1991) *Science* 253:323). These isoforms of APP are generated by alternative splicing of primary transcripts of the APP gene, which is located on human chromosome 21. It is known that the APP isoforms are glycosylated transmembrane proteins (Goldgaber et al. (1987) *Science* 235:877), and that two of the isoforms APP751 and APP770, have a protease inhibitor domain that is homologous to the Kunitz type of serine protease inhibitors. The β-amyloid protein segment comprises approximately half of the transmembrane domain and approximately the first 28 amino acids of the extra cellular domain of an APP isoform.

Proteolytic processing of APP in vivo is a normal physiological process. Carboxy-terminal truncated forms of APP695, APP751, and APP770 are present in brain and cerebrospinal fluid (Palmert et al. (1989) *Proc. Natl. Acad. Sci.* (U.S.A.) 86:6338; Weidemann et al. (1989) *Cell* 57:115) and result from cleavage of the APP isoform at a constitutive cleavage site within the β-amyloid protein peptide domain of an APP isoform (Esch et al. (1990) *Science* 248:1122). Normal proteolytic cleavage at the constitutive cleavage site yields a large (approximately 100 kD) soluble, N-terminal fragment that contains the protease inhibitor domain in some isoforms, and a 9 kD membrane-bound, C-terminal fragment that includes most of the β-amyloid protein domain.

Generation of pathogenic β-amyloid protein appears to be the result of aberrant proteolytic processing of APP, such that normal cleavage at the constitutive site within the β-amyloid protein domain does not occur, but rather cleavage occurs at two specific sites which flank the β-amyloid protein domain. One of these aberrant cleavage sites is in the transmembrane domain and the other aberrant cleavage site is located approximately at the N-terminus of the first 28 amino acids of the extra cellular domain. Such aberrant proteolytic cleavage produces the β-amyloid protein polypeptide which is prone to forming dense amyloidogenic aggregates that are resistant to proteolytic degradation and removal. The resultant β-amyloid protein aggregates presumably are involved in the formation of the abundant amyloid plaques and cerebrovascular amyloid that are the neuropathological hallmarks of AD. However, the exact aberrant cleavage sites are not always precise; β-amyloid molecules isolated from the brain of a patient with AD show N- and C-terminal heterogeneity. Therefore, the aberrant cleavage pathway may involve either sequence-specific proteolysis followed by exopeptidase activity (creating end-heterogeneity), or may not be sequence-specific.

The APP gene is known to be located on human chromosome 21. A locus segregating with FAD has been mapped to chromosome 21 (St. George Hyslop et al. (1987) *Science* 235:885) close to the APP gene. Recombinants between the APP gene and the AD locus have been previously reported (Schellenberg et al. (1988) *Science* 241:1507). The data appeared to exclude the APP gene as the site of any mutation that might cause FAD (Van Broekhoven et al. (1987) *Nature* 329:153; Tanzi et al. (1987) *Nature* 329:156).

Recombinant DNA technology provides several techniques for analyzing genes to locate possible mutations. For example, the polymerase chain reaction (John Bell (1989) *Immunology Today* 10:351-355) may be used to amplify specific sequences using intronic primers, which can then be analyzed by direct sequencing.

Using such techniques, a single base substitution, a C to T transition at base pair 2149, has been found in part of the sequence of the APP gene in some cases of FAD. This base pair transition leads to an amino acid substitution, i.e., valine to isoleucine at amino acid 717 (APP770) (see Yoshikai et al. (1990) *Gene* 87:257), close to the C-terminus of the β-amyloid protein. This suggests that some cases of AD are caused by mutation in the APP gene, specifically mutations that change codon 717 such that it encodes an amino acid other than valine.

A second APP allelic variant wherein glycine is substituted for valine at codon 717 is now identified, and is so closely linked to the AD phenotype as to indicate that allelic variants at codon 717 of the APP gene, particularly those encoding an amino acid other than valine, and more particularly those encoding an isolcucine, glycine, or phenylalanine, are pathogenic and/or pathognomonic alleles (Chartier-Harlin et al. (1991) *Nature* 353:844).

Proteolysis on either side of the β-amyloid protein region of APP may be enhanced or qualitatively altered by the specific mutations at codon 717, increasing the rate of β-amyloid deposition and aggregation. Such codon 717 mutations may increase β-amyloid formation by providing a poorer substrate for the main proteolytic pathway (cleavage at the constitutive site) or a better substrate for a competing, alternative cleavage pathway (at aberrant cleavage sites).

There are several disease states which give rise to progressive intellectual deterioration closely resembling the dementia associated with AD for which treatment is available. A further diagnostic test for AD would therefore provide a valuable tool in the diagnosis and treatment of these other conditions, by way of being able to exclude AD.

Also important is the development of experimental models of AD that can be used to define further the underlying biochemical events involved in AD pathogenesis. Such models could be employed to screen for agents that alter the degenerative course of AD. For example, a model system of AD could be used to screen for environmental factors that induce or accelerate the pathogenesis of AD. In contradistinction, an experimental model could be used to screen for agents that inhibit, prevent, or reverse the progression of AD. Such models could be employed to develop pharmaceuticals that are effective in preventing, arresting, or reversing AD.

The present invention provides the discovery of additional heretofore unknown mutations in β-amyloid protein. These mutations can be utilized advantageously to detect, treat and screen in subjects and model systems.

SUMMARY OF THE INVENTION

The invention provides an isolated nucleic acid characteristic of human amyloid precursor protein 770 including the nucleotides encoding codon 670 and 671, wherein the nucleic acid encodes an amino acid other than lysine at codon 670 and/or an amino acid other than methionine at codon 671. Also provided is a method of diagnosing or predicting a predisposition to AD, comprising detecting in a sample from a subject the presence of a mutation at a nucleotide position corresponding to codons 670 and/or 671 of amyloid precursor protein or fragment thereof, the presence of the mutation indicating the presence of or a predisposition to AD.

DETAILED DESCRIPTION OF THE INVENTION

Figure 1A:
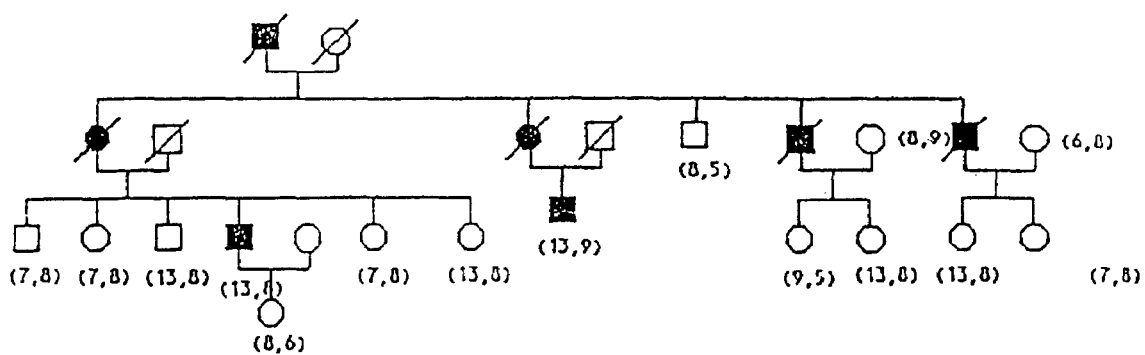
FIGS. 1a and 1b illustrate two related pedigrees in which early onset AD is apparently inherited as an autosomal dominant disorder. +/− refer to presence/absence of mutation. GT12 alleles are in parentheses. The average age of onset in this family is 55 years. Black symbols denote affected individuals and oblique lines indicate deceased individuals. Females are denoted by circles and males by squares. Triangles are used in the present generation to preserve anonymity. For f139, samples were available from the 7 individuals whose genotypes (presence or absence of the mutation) are illustrated, and for f144 samples were available from 15 individuals whose genotypes at GT12 are shown.
Figure 1B:
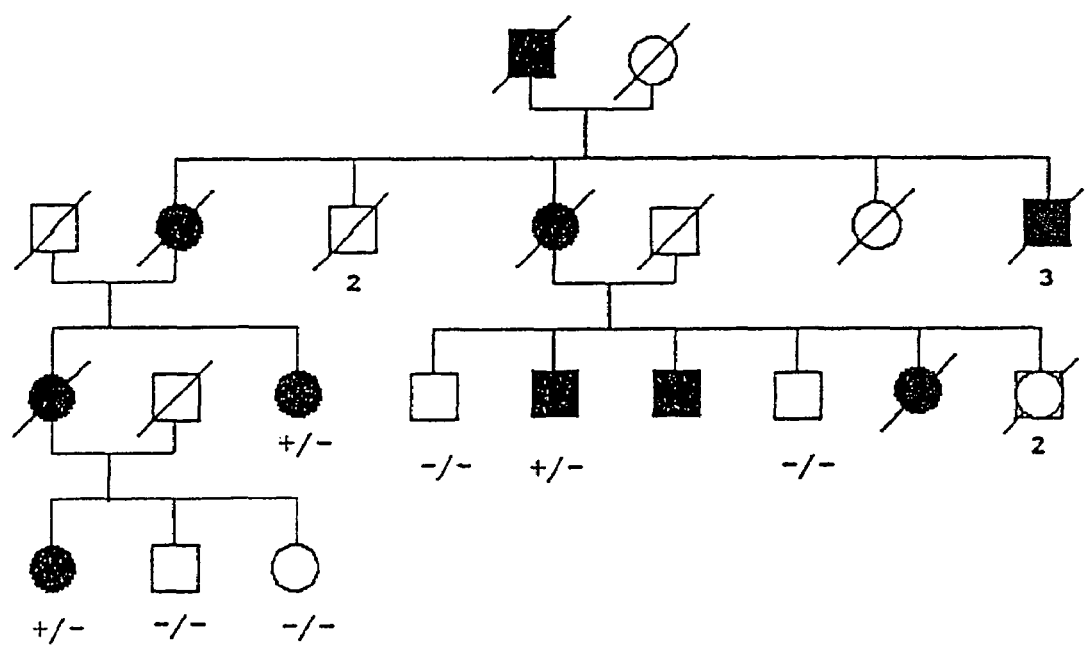

The invention provides an isolated nucleic acid characteristic of human amyloid precursor protein including the nucleotides encoding codon 670 and 671 of human amyloid precursor protein 770, wherein the nucleic acid encodes an amino acid other than lysine at codon 670 and/or an amino acid other than methionine at codon 671. In one embodiment, the nucleic acid encodes asparagine at codon 670 and leucine at codon 671.

The invention also provides an isolated nucleic acid complementary to the nucleic acid of the invention. The isolated nucleic acid can be labeled with a detectable moiety. The isolated nucleic acid can encode, for example, β-amyloid protein and the entire human amyloid precursor protein 770. In addition, the isolated nucleic acid can further encode an amino acid other than valine at codon 717. The invention also provides polypeptides encoded by these nucleic acids.

Further, the invention provides an antibody specifically reactive with the polypeptides of the invention. Thus, antibodies which react with the unique epitope created by the amino acid other than lysine at codon 670 and/or other than methionine at position 671 are provided.

Vectors comprising the nucleic acids of the invention are also provided. These vectors can be placed in a host capable of expressing the characteristic portion of human amyloid precursor protein.

The invention also provides a method of diagnosing or predicting a predisposition to AD. The method comprises detecting in a sample from a subject the presence of a mutation in a human amyloid precursor protein at a nucleotide position corresponding to codons 670 and/or 671 of amyloid precursor protein 770 or fragment thereof, the presence of the mutation indicating the presence of or a predisposition to AD. In one embodiment, the sequence mutation is a nucleotide substitution, wherein codon 670 encodes asparagine and/or codon 671 encodes leucine. As discussed below in greater detail, the mutation can be detected by many methods. For example, the detecting step can comprise combining a nucleotide probe capable of selectively hybridizing to a nucleic acid containing the mutation with a nucleic acid in the sample and detecting the presence of hybridization. Additionally, the detecting step can comprise amplifying the nucleotides of the mutation and detecting the presence of the mutation in the amplified product. Further, the detecting step can comprise selectively amplifying the nucleotides of the mutation and detecting the presence of amplification. Finally, the detecting step can comprise detecting the loss of a restriction fragment length created by an MboII enzyme digest of the nucleotides of the mutation.

The invention also provides a transgenic non-human animal containing, in a germ or somatic cell, the mutated nucleic acid of the invention, wherein the animal expresses a human amyloid precursor protein or fragment thereof which encodes an amino acid other than lysine at codon 670 and/or an amino acid other than methionine at codon 671. Preferably, the animal expresses neuropathological characteristics of AD. These animals can also have a mutation at position 717 wherein the animal expresses a human amyloid precursor protein or fragment thereof which encodes an amino acid other than lysine at codon 670 and/or an amino acid other than methionine at codon 671 and an amino acid other than valine at codon 717.

The invention also provides a host containing the nucleic acid of claim 1, which host expresses a human amyloid precursor protein or fragment thereof which encodes an amino acid other than lysine at codon 670 and/or an amino acid other than methionine at codon 671. Preferably, the host is an immortalized cell line. This host can also contain the mutation at codon 717 whereby the host expresses a human amyloid precursor protein or fragment thereof which encodes an amino acid other than lysine at codon 670 and/or an amino acid other than methionine at codon 671 and an amino acid other than valine at codon 717. The invention also provides a method of screening for an agent capable of treating AD. The method comprises contacting these transgenic animals or host cell lines with the agent and monitoring the expression, processing or deposition of amyloid precursor protein or fragments thereof.

As used herein, "isolated" means free of at least some of the contaminants associated with the nucleic acid or polypeptides occurring in a natural environment.

As used here, "nucleic acid characteristic of human amyloid precursor protein" refers to a nucleic acid which has sufficient nucleotides surrounding the codons at position 670 and 671 of human amyloid precursor protein 770 to distinguish the nucleic acid from nucleic acids encoding non-related proteins. The specific length of the nucleic acid is a matter of routine choice based on the desired function of the sequence. For example, if one is making probes to detect the mutation in either codon 670 and/or 671, the length of the nucleic acid will be smaller, but must be long enough to prevent hybridization to the desired background sequences. However, if the desired hybridization is to a nucleic acid which has been amplified, background hybridization is less of a concern and a smaller probe can be used. In general, such a probe will be between 10 and 100 nucleotides, especially between 10 and 40 nucleotides in length.

Likewise, polypeptides encoded by the nucleic acids of the invention can be variable depending on the desired function of the polypeptide While smaller fragments can work, generally to be useful, e.g., immunogenic, the polypeptide must be of at least 8 amino acids and not more than 10,000 amino acids. This polypeptide contains an amino acid internal sequence (listed in order from amino- to carboxy-terminal direction):

-Ser-Glu-Val-X-X-Asp-Ala-Glu- [SEQ ID NO1]

where the X at position 3 is any of the twenty conventional amino acids except lysine, particularly asparagine, and where the X at position 4 is any of the twenty conventional amino acids except methionine, particularly leucine. The amino and carboxy ends of this core sequence can include any number of additional amino acids from the APP sequence. Thus, "fragment" can be a truncated APP isoform or a modified APP isoform (as by amino acid substitutions, deletions, or additions). This definition recognizes that APP is a single gene that undergoes alternative splicing to generate several isoforms that are designated by the total number of amino acids in each. Thus, treatment includes various alternatively spliced exons resulting in isoforms of 770, 751, 714, 695, 563 and 365 amino acids.

As used here, "codon 670 and/or codon 671" refers to the codons (i.e., the tri-nucleotide sequence) that encode the 670th and 671st amino acid positions in APP770, or the amino acid position in an APP fragment that corresponds to the 670th or 671st positions in APP770. For example, a 670 residue long fragment that is produced by truncating APP770 by removing the 100 N-terminal amino acids has its 570th amino acid position corresponding to codon 670. In fact, as used herein, codon 670 refers to the codon that encodes the 651st amino acid residue of APP751 and the 595th amino acid residue of APP695. In addition, codon 670 and/or 671 refers to the complementary sequence on the antisense strand.

As used herein, the term "mutant" refers specifically to a mutation at codons 670/671 (as referenced by the amino acid sequence in APP770) of the APP gene, such that codon 670 encodes one of the nineteen amino acids that are not lysine (i.e., glycine, methionine, alanine, serine, isoleucine; leucine, threonine, proline, histidine, cysteine, tyrosine, phenylalanine, glutamic acid, tryptophan, arginine, aspartic acid, asparagine, valine, and glutamine), but preferably asparagine, and such that codon 671 encodes one of the nineteen amino acids that are not methionine (i.e., glycine, lysine, alanine, serine, isoleucine, leucine, threonine, proline, histidine, cysteine, tyrosine, phenylalanine, glutamic acid, tryptophan, arginine, aspartic acid, asparagine, valine, and glutamine), but preferably leucine. Thus, a mutant APP770 polypeptide is an APP770 polypeptide that has an amino acid residue at position 670 that is not lysine and or an amino acid residue at position 671 that is not methionine. Other mutant APP isoforms comprise a non-lysine amino acid at the amino acid residue position that corresponds to codon 670 (i.e., that is encoded by codon 670) or a non-methionine amino acid at the amino acid residue position that corresponds to codon 671 (i.e., that is encoded by codon 671). Similarly, a mutant APP allele or a variant APP codon 670 or 671 allele is an APP allele that encodes a non-lysine amino acid at the amino acid residue position that corresponds to codon 670 (i.e., that is encoded by codon 670) or encodes a non-methionine amino acid at the amino acid residue position that corresponds to codon 671 (i.e., that is encoded by codon 671).

It is apparent to one of skill in the art that nucleotide substitutions, deletions, and additions may be incorporated into the polynucleotides of the invention. However, such nucleotide substitutions, deletions, and additions should not substantially disrupt the ability of the polynucleotide to hybridize to one of the polynucleotide sequences under hybridization conditions that are sufficiently stringent to result in specific hybridization.

"Specific hybridization" is defined herein as the formation of hybrids between a probe nucleic acid (e.g., a nucleic acid which may include substitutions, deletions, and/or additions) and a specific target nucleic acid (e.g., a nucleic acid having the sequence), wherein the probe preferentially hybridizes to the specific target such that, for example, a band corresponding to a variant APP allele or restriction fragment thereof can be identified on a Southern blot, whereas a corresponding wild-type APP allele (i.e., one that encodes lysine at codon 670 and methionine at codon 671) is not identified or can be discriminated from a variant APP allele on the basis of signal intensity. Hybridization probes capable of specific hybridization to detect a single-base mismatch may be designed according to methods known in the art and described in Maniatis et al. (1989) *Molecular Cloning: A Laboratory Manual*, 2nd Ed., Cold Spring Harbor Laboratory, Cold Spring Harbor, N.Y.; Berger and Kimmel (1987) "Guide to Molecular Cloning Techniques," *Methods in Enzymology*, Volume 152Academic Press, Inc., San Diego, Calif.; Gibbs et al. (1989) *Nucleic Acids Res.* 17:2437; Kwok et al. (1990) *Nucleic Acids Res.* 18:999; and Miyada et al. (1987) *Methods Enzymol.* 154:94.

The vectors for expressing the polypeptides of the invention require that the nucleic acid be "operably linked." A nucleic acid is operably linked when it is placed into a functional relationship with another nucleic acid sequence. For instance, a promoter or enhancer is operably linked to a coding sequence if it affects the transcription of the sequences. Operably linked means that the DNA sequences being linked are contiguous and, where necessary to join two protein coding regions, contiguous and in reading frame.

The term "agent" is used herein to denote a chemical compound, a mixture of chemical compounds, a biological macromolecule, or an extract made from biological materials such as bacteria, plants, fungi, or animal (particularly mammalian) cells or tissues. Agents are evaluated for potential biological activity by inclusion in screening assays described herein below.

As used here, the terms "label" or "labeled" refer to incorporation of a radio labeled nucleotide or by enzymatic or fluorescent marker. DNA or RNA are typically labeled by incorporation of a radio-labeled nucleotide (H3, C14, S35, P32) or a biotinylated nucleotide that can be detected by marked avidin (e.g., avidin containing a fluorescent marker or enzymatic activity) or digoxygeninylated nucleotide that can be detected by marked specific antibody.

DESCRIPTION OF THE PREFERRED EMBODIMENT

The following examples are intended to illustrate but not limit the invention. While they are typical of those that might be used, other procedures known to those skilled in the art may be alternatively employed.

Detection of Mutant Codon 670/671 APP Alleles

F139 and F144 are two large Swedish families which originate from the same county. They were specifically ascertained for genetic analysis. We tested F144 for linkage between AD and GT12 (FIG. 1a). A lod value of 2.34 with no recombination was obtained between GT12 and AD. Linkage analysis of 1000 simulated pedigrees (Weeks et al. (1990) *Am. J. Hum. Genet.* 47:A204 (Suppl.)) (of identical structure to F144) showed that this value was likely to occur less than one time in 100 if the marker and the disease were unlinked. We therefore sequenced exons 16 and 17 of the APP gene as these encode β-amyloid protein. Two base pair transversions (G->T and A->C) were observed in affected individuals in both families in exon 16 at codons 670 and 671 (APP 770 transcript). These changes predict lysine to asparagine and methionine to leucine substitutions in the intact protein. In addition, the codon 670 mutation causes the loss of an MboII recognition site. Using this, we screened all available members of both F144 and F139by PCR amplification of exon 16 and digestion with this enzyme. All affected members of both families had lost the MboII cut site. The presence of the mutation was confirmed by direct sequencing of four individuals. This mutation is linked to the disease in these families with a lod score of 4.36 with no recombination. Taken with the fact that we could not detect this variant in 50 normal chromosomes, this demonstrates that this mutation is pathogenic of the dementia in these families.

Therefore, the method of the invention involves identifying a genetic alteration at amino acids 670 or 671 or both which may cause the consensus lysine or methionine (respectively) to be changed. This will generally be performed on specimens removed from the subject.

This mutation differs from previous mutations causing AD in that it is at the N-terminus of deposited β-amyloid protein rather than the C-terminus. The processing of APP has not been fully elucidated but two pathways have been postulated as important (Hardy and Higgins (1992) *Science* 256:184-5). The main proteolytic cleavage by "secretase" normally cuts APP through β-amyloid (Esch et al. (1990) *Science* 248: 1122-1124; Anderson et al. (1991) *Neurosci. Letts.* 128:126-128), thus preventing its formation. An alternative endosomal/lysosomal pathway (Estus et al. (1992) *Science* 255:726-728; Golde et al. (1992) *Science* 255:728-730) apparently produces β-amyloid containing fragments and involves cleavage at or close to the site of the codon 670/671 mutation reported here.

APP717 variants have been suggested to produce amyloidogenic fragments by a number of mechanisms. Thus, they have been postulated to inhibit degradation of amyloidogenic fragments of APP directly or to alter cellular addressing of the APP molecule so that it is mismetabolised, or to alter APP expression levels by effecting mRNA stability (Goate et al. (1991) *Nature* 349:704-706; Chartier Harlin et al. (1991) *Nature* 353:844-846; and Hardy and Higgins (1992) *Science* 256:184-5).

If the dementia-causing mutations in APP all have a related action which underlies their pathogenicity, then the mutations reported here (APP670/1) would also be expected to have their effect through one of the above mechanisms. The position of this mutation right at the N-terminal of β-amyloid protein is most consistent with the notion that the AD causing-mutations directly inhibit the degradation of preamyloidogenic fragments. It seems likely that given the relatively late age of onset of disease development in humans with either codon 717 or 670/1 variants, transgenic animals with any of these mutations may not develop significant pathology. An important consequence of this mutation can be its combination with pathogenic codon 717 variants to increase the likelihood of producing Alzheimer-like pathology in transgenic animals.

Therefore, genetic alterations in the APP gene which result in altered degradative properties are particularly important in the application of the invention. There are several methodologies available from recombinant DNA technology which may be used for detecting and identifying a genetic mutation responsible for AD. These include, for example, direct probing, polymerase chain reaction (PCR) methodology, restriction fragment length polymorphism (RFLP) analysis and single stand conformational analysis (SSCA). However, any other known methods or later discovered methods can likewise be used to detect the mutations. Once the location of the 670/1 mutations are known and associated with AD, the methods to detect the mutations are standard in the art. The sequence of various nucleotide probes can be determined from the sequence of APP, especially the sequences surrounding 670/1. The sequence of APP is set forth in Yoshikai et al. (1990) "Genomic organization of the human amyloid beta-protein precursor gene," *Gene* 87:257-263.

Detection of point mutations using direct probing involves the use of oligonucleotide probes which may be prepared synthetically or by nick translation. The DNA probes may be suitably labeled using, for example, a radio label, enzyme label, fluorescent label, biotin-avidin label and the like for subsequent visualization in the example of Southern blot hybridization procedure. The labeled probe is reacted with a bound sample DNA, e.g., to a nitrocellulose sheet under conditions such that only fully complementary sequences hybridize. The areas that carry DNA sequences complementary to the labeled DNA probe become labeled themselves as a consequence of the reannealing reaction. The areas of the filter that exhibit such labeling may then be visualized, for example, by autoradiography. The labeled probe is reacted with a DNA sample bound to, for example, nitrocellulose under conditions such that only fully complementary sequences will hybridize. Tetra-alkyl ammonium salts bind selectively to A-T base pairs, thus displacing the dissociation equilibrium and raising the melting temperature. At 3M Me 4NCl this is sufficient to shift the melting temperature to that of G-C pairs. This results in a marked sharpening of the melting profile. The stringency of hybridization is usually 5° C. below the Ti (the irreversible melting temperature of the hybrid formed between the probe and its target sequence) for the given chain length. For 20 mers the recommended hybridization temperature is 58° C. The washing temperatures are unique to the sequence under investigation and need to be optimized for each variant.

Alternative probing techniques, such as ligase chain reaction (LCR), involve the use of mismatch probes, i.e., probes which are fully complementary with the target except at the point of the mutation. The target sequence is then allowed to hybridize both with oligonucleotides which are fully complementary and have oligonucleotides containing a mismatch, under conditions which will distinguish between the two. By manipulating the reaction conditions, it is possible to obtain hybridization only where there is full complementarity. If a mismatch is present there is significantly reduced hybridization.

The polymerase chain reaction (PCR) is a technique that amplifies specific DNA sequences with remarkable efficiency. Repeated cycles of denaturation, primer annealing and extension carried out with polymerase, e.g., a heat stable enzyme Taq polymerase, leads to exponential increases in the concentration of desired DNA sequences. Given a knowledge of the nucleotide sequence encoding the precursors of amyloid protein of AD (Kang et al. *Nature* 197:325, 733-736, and Yoshikai above), synthetic oligonucleotides can be prepared which are complementary to sequences which flank the DNA of interest. Each oligonucleotide is complementary to one of the two strands. The DNA is denatured at high temperatures (e.g., 95° C.) and then reannealed in the presence of a large molar excess of oligonucleotides. The oligonucleotides, oriented with their 3' ends pointing towards each other, hybridize to opposite strands of the target sequence and prime enzymatic extension along the nucleic acid template in the presence of the four deoxyribonucleotide triphosphates. The end product is then denatured again for another cycle. After this three-step cycle has been repeated several times, amplification of a DNA segment by more than one million-fold can be achieved. The resulting DNA may then be directly sequenced in order to locate any genetic alteration. Alternatively, it may be possible to prepare oligonucleotides that will only bind to altered DNA, so that PCR will only result in multiplication of the DNA if the mutation is present. Following PCR, direct visualization or allele-specific oligonucleotide hybridization (Dihella et al. (1988) *Lancet* 1:497) may be used to detect the AD point mutation. Alternatively, an adaptation of PCR called amplification of specific alleles (PASA) can be employed; this uses differential amplification for rapid and reliable distinction between alleles that differ at a single base pair.

In yet another method, PCR may be followed by restriction endonuclease digestion with subsequent analysis of the resultant products. The substitution of T for G at base pair 2010, found as a result of sequencing exon 16, destroys an MboII restriction site. The destruction of this restriction endonuclease recognition site facilitates the detection of the AD mutation using RFLP analysis or by detection of the presence or absence of a polymorphic MboII site in a PCR product that spans codon 670.

In general, primers for PCR and LCR are usually about 20 bp in length and the preferable range is from 15-25 bp. Better amplification is obtained when both primers are the same length and with roughly the same nucleotide composition. Denaturation of strands usually takes place at 94° C. and extension from the primers is usually at 72° C. The annealing temperature varies according to the sequence under investigation. For exon 16, with the primers we have designed, the optimum annealing temperature is 58° C. The reaction times are: 20 mins denaturing; 35 cycles of 2 min, 1 min, 1 min for annealing, extension and denaturation; and finally a 5 min extension step.

For RFLP analysis, DNA is obtained, for example from the blood of the subject suspected of having AD and from a normal subject, is digested with the restriction endonuclease MboII and subsequently separated on the basis of size by agarose gel electrophoresis. The Southern blot technique can then be used to detect, by hybridization with labeled probes, the products of endonuclease digestion. The patterns obtained from the Southern blot can then be compared. Using such an approach, DNA spanning an Alzheimer's mutation that creates or removes a restriction site at codon 670 or 671, such as the MboII site, is detected by determining the number of bands detected and comparing this number to a reference allele that has a codon 670 allele that encodes lysine or a codon 671 allele that encodes methionine.

Similar creation of additional restriction sites by nucleotide substitutions within codons 670 or 671, wherein the codon 670 encodes an amino acid other than lysine or codon 671 encodes an amino acid other than methionine, can be readily calculated by reference to the genetic code and a list of nucleotide sequences recognized by restriction endonucleases (*Promega Protocols and Applications Guide* (1991) Promega Corporation, Madison, Wis.).

Single strand conformational analysis (SSCA) (Orita et al. (1989) *Genomics* 5:874-879 and Orita et al. (1990) *Genomics* 6:271-276) offers a relatively quick method of detecting sequence changes which may be appropriate in at least some instances.

PCR amplification of specific alleles (PASA) is a rapid method of detecting single-base mutations or polymorphisms (Newton et al. (1989) *Nucleic Acids Res.* 17:2503; Nichols et al. (1989) *Genomics* 5:535; Okayama et al. (1989) *J. Lab. Clin. Med.* 114:105; Sarkar et al. (1990) *Anal. Biochem.* 186: 64; Sommer et al. (1989) *Mayo Clin. Proc.* 64:1361; Wu (1989) *Proc. Natl. Acad. Sci.* (*U.S.A.*) 86:2757; and Dutton et al. (1991) *Biotechniques* 11:700. PASA (also known as allele specific amplification) involves amplification with two oligonucleotide primers such that one is allele-specific. The desired allele is efficiently amplified, while the other allele(s) is poorly amplified because it mismatches with a base at or near the 3' end of the allele-specific primer. Thus, PASA or the related method of PAMSA may be used to specifically amplify one or more variant APP codon 670 or 671 alleles. Where such amplification is done on genetic material (or RNA) obtained from an individual, it can serve as a method of detecting the presence of one or more variant APP codon 670 or 671 alleles in an individual.

Similarly, a method known as ligase chain reaction (LCR) has been used to successfully detect a single-base substitution in a hemoglobin allele that causes sickle cell anemia (Baany et al. (1991) *Proc. Natl. Acad. Sci.* (*U.S.A.*) 88:189; R. A. Weiss (1991) *Science* 254:1992). LCR probes may be combined or multiplexed for simultaneously screening for multiple different mutations. Thus, one method of screening for variant APP codon 670 or 671 alleles is to multiplex at least one, and preferably all, LCR probes that will detect an APP allele having a codon 670 that does not encode lysine or an APP allele having a codon 671 that does not encode methionine, but that does encode other amino acids. The universal genetic code provides the degenerate sequences of all the encoded non-lysine and non-methionine amino acids, thus LCR probe design for detecting any particular variant codon 670 or 671 (or combination thereof) allele is straightforward, and multiplexed pools of such LCR problems may be selected at the discretion of a practitioner for his particular desired use.

In performing diagnosis using any of the above techniques or variations thereof, it is preferable that several individuals are examined. These may include an unaffected parent, an affected parent, an affected sibling, an unaffected sibling as well as other perhaps more distant family members.

Model Animals and Cell Lines

Having identified specific mutations in codons 670/1 of the β-amyloid gene as a cause of FAD, it is possible, using genetic manipulation, to develop transgenic model systems and/or whole cell systems containing the mutated FAD gene (or a portion thereof) for use, for example, as model systems for screening for drugs and evaluating drug effectiveness. Additionally, such model systems provide a tool for defining the underlying biochemistry of APP and β-amyloid metabolism, which thereby provides a basis for rational drug design.

One type of cell system can be naturally derived. For this, blood samples from an affected subject must be obtained in order to provide the necessary cells which can be permanently transformed into a lymphoblastoid cell line using, for example, Epstein-Barr virus. Once established, such cell lines can be grown continuously in suspension culture and may be used for a variety of in vitro experiments to study APP expression and processing.

Since the FAD mutation is dominant, an alternative method for constructing a cell line is to genetically engineer the mutated gene into an established cell line of choice. Sisodia ((1990) *Science* 248:492-494) has described the insertion of a normal APP gene, by transfection, into mammalian cells.

In yet a further use of the present invention, the mutated gene (i.e., a variant APP codon 670/1 gene) can be excised for use in the creation of transgenic animals containing the mutated gene. For example, an entire human variant APP codon 670/1 allele can be cloned and isolated, either in parts or as a whole, in a suitable cloning vector (e.g., lCharon35, cosmid, retrovirus or yeast artificial chromosome). The vector is selected based on the size of the desired insert and the ability to produce stable chromosome integration.

The human variant APP codon 670/1 gene, either in parts or in whole, can be transferred to a host non-human animal, such as a mouse. As a result of the transfer, the resultant transgenic non-human animal will express one or more variant APP codon 670/1 polypeptides. Preferably, a transgenic non-human animal of the invention will express one or more variant APP codon 670/1 polypeptides in a neuron-specific manner (Wirak et al. (1991) *EMBO* 10:289). This may be accomplished by transferring substantially the entire human APP gene (encoding a codon 670/1 mutant) including the 4.5 kilobase sequence that is adjacent to and upstream of the first major APP transcriptional start site.

Alternatively, one may design mini-genes encoding variant APP codon 670/1 polypeptides. Such mini-genes may contain a cDNA sequence encoding a variant APP codon 670/1 polypeptide, preferably full-length, a combination of APP gene exons, or a combination thereof, linked to a downstream polyadenylation signal sequence and an upstream promoter (and preferably enhancer). Such a mini-gene construct will, when introduced into an appropriate transgenic host (e.g., mouse or rat), express an encoded variant APP codon 670/1 polypeptide, most preferably a variant APP codon 670/1 polypeptide that contains either an asparagine residue at codon 670 and a leucine residue at codon 671 of APP770 or the corresponding position in an APP fragment.

One approach to creating transgenic animals is to target a mutation to the desired gene by homologous recombination in an embryonic stem (ES) cell line in vitro followed by microinjection of the modified ES cell line into a host blastocyst and subsequent incubation in a foster mother (see Frohman and Martin, Cell (1989) 56:145). Alternatively, the technique of microinjection of the mutated gene, or a portion thereof, into a one-cell embryo followed by incubation in a foster mother can be used. Certain possibilities for the general use of transgenic animals, particularly transgenic animals that express a wild-type APP fragment, are disclosed in Wirak et al., the EMBO Journal, 10(2) 289-296 (1991); Schilling et al., Gene 98(2) 225-230 (1991); Quon, et al. (1991) Nature 352:239; Wirak, et al. (1991) Science 253:323; and Kawabata, et al. (1991) Nature 354:476. Alternatively, viral vectors, e.g., Adeno-associated virus, can be used to deliver the mutated gene to the stem cell. In addition, such viral vectors can be used to deliver the mutated gene to a developed animal and then used to screen (Mendelson et al. *Virology* 166:154-165; Wondisford et al. (1988) *Molec. Endocrinol.* 2:32-39 (1988)).

Site-directed mutagenesis and/or gene conversion can also be used to mutate a murine APP gene allele, either endogenous or transfected, such that the mutated allele does not encode lysine/methionine at the codon position in the mouse APP gene that corresponds to codon 670/1 (of APP770) of the human APP gene (such position is readily identified by homology matching of the murine APP gene or APP protein to the human APP gene or APP770 protein). Preferably, such a mutated murine allele would encode asparagine or leucine at the corresponding codon position.

To more accurately model the disease, the combination in transgenic animals of the codon 670/1 and codon 717 mutations in the same animal produced by any of the technologies described above can be utilized. Similarly, cell lines manipulated to include both mutations at codon 717 and codon 670/1 will be of value in modeling the disease and are an important consequence of this invention. The mutations at codon 717 can be produced by the above methods as described for the 670/1 mutation.

Production of Transgenic Animals with Mutant APP Allele

This method refers only to the production of a codon 670/1 mutated allele. However, it is intended that by almost identical means, a mouse with mutations at both codon 670/1 and codon 717 can be produced.

Generation of the constructs: The vector plink can be constructed by cloning polylinker between the PvuII and EcoRI sites of pBR322 such that the HindIII end of the polylinker is adjacent to the PvuII site. The ligation destroys both the EcoR1 and PvuII sites associated with the pBR322 segments. The 700 bp HpaI to EcoR1 fragment of pSV2neo (Southern and Berg (1982) *J. Mol. Appl. Genet.* 1:327-41 that contains the SV40 polyadenylation signal can be cloned into the HpaI to EcoR1 sites of plink to generate pNotSV. The 200 bp XhoI to PstI fragment of pL2 containing the SV40 16S/1gS splice site (Okayama and Berg (1983) *Mol. Cell Biol* 3:280-9) can be isolated, blunted with Klenow, then cloned in to the HpaI site of pNotSV to generate pSplice. The 2.3 kb Nru1 to SpeI fragment of pAPP695 containing the coding region of the cDNA for APP (Tanzi et al. (1987) *Science* 235:80-4, 1987) can be inserted into the NruI to SpeI site of pSplice to generate pd695. The same strategy can be used to generate pd751 using the cDNA for APP751 (Tanzi et al. (1988) *Nature* 331:528-30, 1988). A variety of promotors can be inserted into the pd695 and pd751 vectors by using the unique Nru1 or the HindIII and NruI sites.

Generation of pshAPP695 and pshAPP751: The construct pAmyproBam can be generated by cloning the 1.5 kb Bam H1 fragment of the APPcDNA into the Bam HI site of puc19 xHamy. The 700 bp HindIII to ASP718 fragment of the pAmyproBam (from Sheila Little @ Lilly Research Labs, same fragment as: Salbaum et al. (1988) *EMBO J.* 7:2807-13) can be cloned into the HindIII to Asp718 sites of pd695 and pd751 to yield psyAPP695 and pshAPP751.

pAPP695 and pAPP751: The pAPP695 and pAPP751 vectors can be generated by a 3-way ligation of the 3.0 kb Eco R1 to XhoI fragment of pAmyProBam, the 1.5 kb XhoI to SpeI fragment of APP751cDNA, and the SpeI to Eco R1 site of pd751.

Generation of pNSE751(+47): The pNSE751 (+47) can be constructed using a 3-way ligation of the HindIII to KpnI fragment of pNSE6 (Forss-Petter et al. (1990) *Neuron* 5:187-97). The KpnI to PstY1 fragment of pNSE6 and a partial BamH1 (−47nt relative to the ATG) to HindIII fragment of pAPP751. This can result in the generation of a KpnI fragment that can be cloned into the KpnI sites of pNSE751(+47). The BstY1/Bam fusion results in the loss of both sites.

Generation of pNSE751: This vector is generated by a 4 primer 2-step PCR protocol that results in direct fusion of the NFH initiation codon to the APPcDNA coding region. The fusion can be confirmed by sequence analysis.

Generation of pNSE751-codon670/1: The codon 670/1 mutation can be introduced using a 4 primer 2-PCR protocol (Krummel et al. (1988) *NAR* 16:7351-60). The "inside primers" can contain the mutation. This can result in the generation of BglII to SpeI fragment after digestion, which can contain the codon 670/1 mutation. The BglII to SpeI fragment of pNSE751 can be replaced by the mutated fragment to generate the appropriate vector. The presence of the mutation can be confirmed by sequence analysis of the vectors.

Generation of pNFH751: The human NFH gene can be isolated from a genomic library using a rat NFH cDNA as a probe (Lieberburg et al. (1989) *PNAS USA* 86:2463-7). An SstI fragment can be subcloned into the pSK vector. A pair of PCR primers can be generated to place a NruI site at the 3' end of the 150 bp amplified fragment immediately upstream of the initiation codon of the NFH gene. The 5' end contains a KpnI site 150 nt upstream of the initiation codon. The final construction of pNFH751 can be generated by a 3-way ligation of the 5.5 b HindIII to KpnI fragment of pNFH8.8, the KpnI to NruI PCR generated fragment, and the HindIII to NruI fragment of pd751. The sequence surrounding the PCR generated fusion at the initiation codon can be confirmed by sequence analysis. The codon 670/1 variants of pNFH751 can be generated by substitution of the 600 bp BglII to SpeI fragment from a sequence-confirmed mutated vector for the same fragment of pNFH751. The presence of the mutation can be confirmed by hybridization with the mutated oligomer or by sequence analysis.

Generation of pThy751: The pThy751 vector can be generated by a 3-way ligation: the HmdII to BamH1 fragment of pThy8.2 (isolated from a human generic library), the synthetic fragment ThyAPP, and the HindIII to NruI fragment of pd751.

ThyAPP:

[SEQ ID NO2]
CAGACTGAGATCCCAGAACCCTAGGTCTGACTCTAGGGTCTTGG

Generation of pThyC100: This pThyC100 construct can be generated by a 3-way ligation: the 3.6 kb HindIII to BamH1 fragment of pThy8.2, the synthetic fragment ThyAPP2, and the HindIII to Bg1II fragment of pd751 or pNSE751-codon 670/1 can be ligated to yield pThyc100.

ThyAPP2:

[SEQ ID NO3]
CAGACTGAGATCCCAGAACCGATCCTAGGTCTGACTCTAGGGTCTTGG

The region around the initiation codon was confirmed by sequence analysis.

Preparation of DNA for injection: The transgene for injection can be isolated from the corresponding vector for digestion with NotI and gel electrophoresis. The transgene can be purified by using the gene clean kit (Bio101), then further purified on an Elutip or HPLC purified on a Nucleogen 4000 column.

Microinjection: The transgene can be injected at 2-20 mcg/ml into the most convenient pronucleus of FVB or B6D2F2 one-cell embryos (Hogan et al. (1986) *Manipulating the Mouse Embryo*, Cold Spring Harbor Laboratory, Cold Spring Harbor, N.Y.). The injected embryos can be cultured overnight. Embryos that split to the two-cell stage can be implanted into pseudo-pregnant female CD1 mice. The mice can be weaned at approximately 21 days. Samples of DNA obtained from tail biopsy can be analyzed by Southern blot using a transgene specific probe (usually the SV40 3's splice and polyadenylation signal sequences). Transgenic mice harboring at least one copy of the transgene can be identified.

Therapeutics

Having detected the genetic mutation in the gene sequence coding for β-amyloid protein in an individual not yet showing overt signs of FAD using the method of the present invention, it is possible to employ gene therapy, in the form of gene implants, to prevent the development of the disease.

Additional embodiments directed to modulation of the production of variant APP proteins include methods that employ specific antisense polynucleotides complementary to all or part of a variant APP sequence. Such complementary antisense polynucleotides may include nucleotide substitutions, additions, deletions, or transpositions, so long as specific hybridization to the relevant target sequence, i.e., a variant APP codon 670/1 sequence, is retained as a property of the polynucleotide. Thus, an antisense polynucleotide must preferentially bind to a variant APP (i.e., codon 670 does not encode lysine and/or codon 671 does not encode methionine) sequence as compared to a wild-type APP (i.e., codon 670 and 671 do encode lysine and methionine, respectively). It is evident that the antisense polynucleotide must reflect the exact nucleotide sequence of the variant allele (or wild-type allele where desired) and not a degenerate sequence.

Complementary antisense polynucleotides include soluble antisense RNA or DNA oligonucleotides which can hybridize specifically to a variant APP mRNA species and prevent transcription of the mRNA species and/or translation of the encoded polypeptide (Ching et al. (1989) *Proc. Natl. Acad. Sci. (U.S.A.)* 86:10006-10010; Broder et al. (1990) *Ann. Int. Med.* 113:604-618; Loreau et al. (1990) *FEBS Letters* 274:53-56; Holcenberg et al., WO91/11535; U.S. Ser. No. 07/530,165 ("new human CRIPTO gene"); WO91/09865; WO91/04753; WO90/13641; and EP 386563). The antisense polynucleotides therefore inhibit production of the variant APP polynucleotides. Antisense polynucleotides may preferentially inhibit transcription and/or translation of mRNA corresponding to variant (or wild-type) polypeptides and can inhibit T lymphocyte activation.

Antisense polynucleotides may be produced from a heterologous expression cassette in a transfectant cell or transgenic cell or animal, such as a transgenic neural, glial, or astrocytic cell, preferably where the expression cassette contains a sequence that promotes cell-type specific expression (Wirak et al. (1991) *EMBO* 10:289). Alternatively, the antisense polynucleotides may comprise soluble oligonucleotides that are administered to the external milieu, either in the culture medium in vitro or in the circulatory system or interstitial fluid in vivo. Soluble antisense polynucleotides present in the external milieu have been shown to gain access to the cytoplasm and inhibit translation of specific mRNA species. In some embodiments the antisense polynucleotides comprise methylphosphonate moieties. For general methods relating to antisense polynucleotides, see Antisense RNA and DNA, D. A. Melton, Ed. (1988), Cold Spring Harbor Laboratory, Cold Spring Harbor, N.Y.

Mutant APP Antigens and Monoclonal Antibodies

In yet another aspect of the invention, having detected a genetic alteration in a gene sequence coding for APP, one can obtain samples of the altered β-amyloid protein from the same source. This protein may be derived from the brain tissue of a subject diagnosed as suffering from AD, or more preferably are produced by recombinant DNA methods or are synthesized by direct chemical synthesis on a solid support. Such polypeptides can contain an amino acid sequence of an APP variant allele spanning codon 670 or 671 or both.

Such polypeptide material can be used to prepare antisera and monoclonal antibodies using, for example, the method of Kohler and Milstein ((1975) *Nature* 256:495-497). Such monoclonal antibodies could then form the basis of a diagnostic test.

Such variant APP polypeptides can also be used to immunize an animal for the production of polyclonal antiserum. For general methods to prepare antibodies, see *Antibodies: A Laboratory Manual*, Harlow and Lane (1988), Cold Spring Harbor Laboratory, Cold Spring Harbor, N.Y. For example, a recombinantly produced fragment of a variant APP codon 670/1 polypeptide can be injected into a mouse along with an adjuvant so as to generate an immune response. Murine immunoglobulins which bind the recombinant fragment with a binding affinity of at least $1\times10^7$ m−1 can be harvested from the immunized mouse as an antiserum, and may be further purified by affinity chromatography or other means. Additionally, spleen cells are harvested from the mouse and fused to myeloma cells to produce a bank of antibody-secreting hybridoma cells. The bank of hybridomas can be screened for clones that secrete immunoglobulins which bind the recombinantly produced fragment with an affinity of at least $1\times10^6$ M−1. More specifically, immunoglobulins that bind to the variant APP codon 670/1 polypeptide but poorly or not at all to a wild-type (i.e., codon 670 encodes lysine and codon 671 encodes methionine) APP polypeptide are selected, either by pre-absorption with wild-type APP or by screening of hybridoma cell lines for specific idiotypes that bind the variant but not wild-type.

The nucleic acid sequences of the present invention capable of ultimately expressing the desired variant APP polypeptides can be formed from a variety of different polynucleotides (genomic or cDNA, RNA, synthetic oligonucleotides, etc.) as well as by a variety of different techniques.

As stated previously, the DNA sequences can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired DNA sequences (see, e.g., U.S. Pat. No. 4,704,362).

Polynucleotides encoding a variant APP codon 670/1 polypeptide may include sequences that facilitate transcription (expression sequences) and translation of the coding sequences such that the encoded polypeptide product is produced. Construction of such polynucleotides is well known in the art and is described further in Maniatis et al. (1989) *Molecular Cloning: A Laboratory Manual*, 2nd Ed., Cold Spring Harbor Laboratory, Cold Spring Harbor, N.Y. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

*E. coli* is one prokaryotic host useful particularly for cloning the DNA sequences of the present invention. Other microbial hosts suitable for use include bacilli, such as *Bacillus subtilus*, and other enterobacteriaceae, such as *Salmonella, Serratia*, and various *Pseudomonas* species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation.

Other microbes, such as yeast, may also be used for expression. *Saccharomyces* is a preferred host, with suitable vectors having expression control sequences, such as promoters, including 3-phosphoglycerate kinase or other glycolytic enzymes, and an origin of replication, termination sequences etc. as desired.

In addition to microorganisms, mammalian tissue cell culture may also be used to express and produce the polypeptides of the present invention (see Winacker (1987) "From Genes to Clones," VCH Publishers, New York, N.Y.). Eukaryotic cells are actually preferred, because a number of suitable host cell lines capable of secreting intact human proteins have been developed in the art, and include the CHO cell lines, various COS cell lines, LeLa cells, myeloma cell lines, Jurkat cells, etc. Expression vectors for these cells can include expression control sequences, such as an origin of replication, a promoter, an enhancer (Quenn et al. (1986) *Immunol. Rev.* 89:49-68), and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the DNA segments of interest (e.g., polypeptides encoding a variant APP polypeptide) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

The method lends itself readily to the formulation of test kits which can be utilized in diagnosis. Such a kit would comprise a carrier compartmentalized to receive in close confinement one or more containers wherein a first container may contain suitably labeled DNA probes. Other containers may contain reagents useful in the localization of the labeled probes, such as enzyme substrates. Still other containers may contain restriction enzymes (such as MboII), buffers etc., together with instructions for use.

Throughout this application various publications are referenced. The disclosures of these publications in their entireties are hereby incorporated by reference into this application in order to more fully describe the state of the art to which this invention pertains.

The preceding examples are intended to illustrate but not limit the invention. While they are typical of those that might be used, other procedures known to those skilled in the art may be alternatively employed.

nucleotides encoding codon 670, 671 and 717 of human amyloid precursor protein 770, or encoding the codons corresponding to these in other isoforms of APP, operably linked to a promoter, wherein the nucleic acid encodes an amino acid other than lysine at codon 670 and/or an amino acid other than methionine at codon 671 and an amino acid other than valine at codon 717 and, wherein the mouse expresses a human

---

---

What is claimed is:

1. A transgenic mouse whose genome comprises a nucleic acid encoding human amyloid precursor protein including the nucleotides encoding codon 670 and 671 of human amyloid precursor protein 770, or encoding the codons corresponding to these in other isoforms of APP, operably linked to a promoter, wherein the nucleic acid encodes an amino acid other than lysine at codon 670 and/or an amino acid other than methionine at codon 671 and, wherein the mouse expresses a human amyloid precursor protein or fragment thereof which has an amino acid other than lysine at codon 670 and/or an amino acid other than methionine at codon 671.

2. The mouse of claim 1, wherein the mouse forms amyloidogenic aggregates in its brain.

3. A transgenic mouse whose genome comprises, a nucleic acid encoding human amyloid precursor protein including the nucleotides encoding codon 670, 671 and 717 of human amyloid precursor protein 770, or encoding the codons corresponding to these in other isoforms of APP, operably linked to a promoter, wherein the nucleic acid encodes an amino acid other than lysine at codon 670 and/or an amino acid other than methionine at codon 671 and an amino acid other than valine at codon 717 and, wherein the mouse expresses a human amyloid precursor protein or fragment thereof which has an amino acid other than lysine at codon 670 and/or an amino acid other than methionine at codon 671 and an amino acid other than valine at codon 717.

4. The mouse of claim 3, wherein the mouse exhibits Alzheimer's disease pathology.

5. A method of screening for an agent for treating Alzheimer's disease comprising contacting the mouse of claim 2 with the agent and monitoring the expression, processing or deposition of amyloid precursor protein or fragments thereof.

6. A method of screening for an agent treating Alzheimer's disease comprising contacting the mouse of claim 4 with the agent and monitoring the expression, processing or deposition of amyloid precursor protein or fragments thereof.

* * * * *